US00PP12662P2

(12) United States Plant Patent
Heemskerk

(10) Patent No.: US PP12,662 P2
(45) Date of Patent: May 28, 2002

(54) HOSTA PLANT NAMED 'WHITE TRIUMPHATOR'

(75) Inventor: Gerard Heemskerk, Noordwijk (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/642,988

(22) Filed: Aug. 22, 2000

(51) Int. Cl.[7] ..... A01H 5/00
(52) U.S. Cl. ..... Plt./353
(58) Field of Search ..... Plt./353

(56) References Cited

U.S. PATENT DOCUMENTS

PP2,467 P * 1/1965 Grullemans ..... Plt./353

OTHER PUBLICATIONS

UPOV–ROM GTITMComputer Database, GTI JOUVE retrieval software, citations for 'White Triumphator' 2001/02.*

* cited by examiner

*Primary Examiner*—Bruce R. Campell
*Assistant Examiner*—Wendy A. Baker
(74) *Attorney, Agent, or Firm*—C. A. Whealy

(57) ABSTRACT

A distinct cultivar of Hosta plant named 'White Triumphator', characterized by its medium green leaf color; relatively compact growth habit; and white-colored flowers that are positioned above the foliage on strong, straight and erect scapes.

2 Drawing Sheets

BACKGROUND OF THE INVENTION

The present Invention relates to a new and distinct cultivar of Hosta plant, botanically known as *Hosta rectifolia,* and hereinafter referred to by the cultivar name White Triumphator.

The new Hosta is a product of a planned breeding program conducted by the Inventor in a controlled environment in Noordwijk, The Netherlands. The new Hosta was discovered and selected by the Inventor in a seed bed of sown seed from various crosses of unidentified *Hosta rectifolia* selections. The new Hosta was selected in 1993 as an individual seedling on the basis of its straight scapes, the length of its scapes and unique white-colored flowers.

Asexual reproduction of the new cultivar by divisions harvested in Noordwijk, The Netherlands, has shown that the unique features of this new Hosta are stable and reproduced true to type in successive generations.

SUMMARY OF THE INVENTION

Plants of the cultivar White Triumphator have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'White Triumphator'. These characteristics in combination distinguish 'White Triumphator' as a new and distinct cultivar:

1. Medium green leaf color.
2. Relatively compact growth habit.
3. White-colored flowers that are positioned above the foliage on strong, straight and erect scapes.

Plants of the new Hosta can be compared to plants of the variegated *Hosta rectifolia* cultivar Tall Boy, not patented.

Compared to plants of the cultivar Tall Boy, plants of the new Hosta have straight scapes, are more proportional, and have white-colored flowers.

BRIEF DESCRIPTION OF THE PHOTOGRAPHS

The accompanying colored photographs illustrate the overall appearance of the new Hosta, showing the colors as true as it is reasonably possible to obtain in colored reproductions of this type. Colors in the photographs may differ slightly from the color values cited in the detailed botanical description which more accurately describe the actual colors of the new Hosta.

The photograph on the first sheet comprises a side perspective view of a typical flowering plant of 'White Triumphator' grown in a container.

The photograph on the second sheet is a close-up view of typical flowers of 'White Triumphator'.

DETAILED BOTANICAL DESCRIPTION

In the following description, color references are made to The Royal Horticultural Society Colour Chart except where general terms of ordinary dictionary significance are used. Plants used for the following description were about 40 weeks old and grown in containers under field conditions which closely approximate commercial production conditions during the spring and summer in Noordwijk, The Netherlands.

Botanical classification: *Hosta rectifolia* cultivar White Triumphator.

Parentage: Cross-pollination of unidentified selections of *Hosta rectifolia,* not patented.

Propagation:

*Type cutting.*—By divisions.

*Rooting time.*—Divisions harvested in the spring develop roots in about 40 days at 15 to 20° C.

*Root description.*—Fleshy.

Plant description:

*Form.*—Perennial flowering plant; initailly upright becoming outwardly arching as leaves develop; inverted triangle. Moderately clumping: Appropriate for 17-cm containers.

*Crop time.*—After rooting, about 40 weeks are required to produce finished flowering plants in 17-cm containers.

*Plant height.*—From soil level to top of leaf plane: About 40 cm. From soil level to top of flowering stems: About 100 cm.

*Plant diameter.*—About 60 cm.

*Vigor.*—Moderately vigorous.

*Foliage description.*—Leaves basal, simple, generally symmetrical, and long-persisting. Length: About 18 cm. Width: About 11 cm. Shape: Ovate. Apex: Acute to abruptly acute. Base: Cuneate. Margin: Entire. Texture: Glabrous, dull to slightly glossy. Petiole: Length: About 22 cm. Diameter: About 1.2 cm. Color: Young foliage and petiole, upper surface: 137A to 146A. Young foliage and petiole, lower surface: 191A. Mature foliage and petiole, upper surface: 144A to 146B. Mature foliage and petiole, lower surface: 191A to 191B.

Flower description:

*Appearance.*—Single campanulate to funnelform flowers with fused perianth arranged on one-sided racemes. Flowering stems arise from leaf axils. Typically two flowering stems per plant. Flowers persistent.

*Quantity of flowers.*—About 20 flowers per raceme.

*Natural flowering season.*—Summer in the Netherlands; flowering continuous.

*Fragrance.*—Very faint, sweet, pleasant.

*Flower longevity.*—About 4 to 7 days.

*Flower size.*—Length: About 4.5 cm. Diameter: About 5 cm.

*Flower buds* (*about* 3 *days before opening*).—Length: About 3 cm. Diameter: About 8 mm. Shape: Oblanceolate. Color: Base, 155C; apex, 155A.

*Perianth.*—Arrangement: Three interior and three exterior tepals; fused. Tepal length: About 5 cm. Tepal width: About 1.2 cm. Tepal shape: Elongated; apex, acute; margin, entire. Tepal texture: Smooth; glabrous. Tepal color: When opening, upper and lower surfaces: Close to 155D. Fully opened, upper and lower surfaces: Close to 155D; with development, 155C.

*Floral bracts.*—Arrangement: At pedicel base. Length: About 2 cm. Width: About 8 mm. Shape: Lanceolate. Color: 145C to 145D.

*Pedicel.*—Length: About 1.5 cm. Angle: Erect to about 50 to 60° from vertical; bent with weight of flower. Strength: Moderate to strong. Color: 155A to 155C.

*Scape.*—Length: About 60 cm. Aspect: Mostly upright; straight. Texture: Smooth; glaucous. Color: 138B to 139C.

*Reproductive organs.*—Stamens: Quantity: Six; dorsifixed. Anther size: About 3 by 1 mm. Anther color: 15B. Pollen amount: Scarce. Pistils: Quantity: One. Pistil length: About 4 cm. Style length: About 3.8 cm. Style color: 150D; base, 145B. Stigma color: 160C. Ovary color: 145A.

*Seed description.*—Length: About 4 mm. Diameter: About 1 mm. Color: Almost black.

Disease resistance: Plants of the new Hosta have not been noted to be resistant to pathogens common to Hosta.

It is claimed:

1. A new and distinct cultivar of Hosta plant named 'White Triumphator', as illustrated and described.

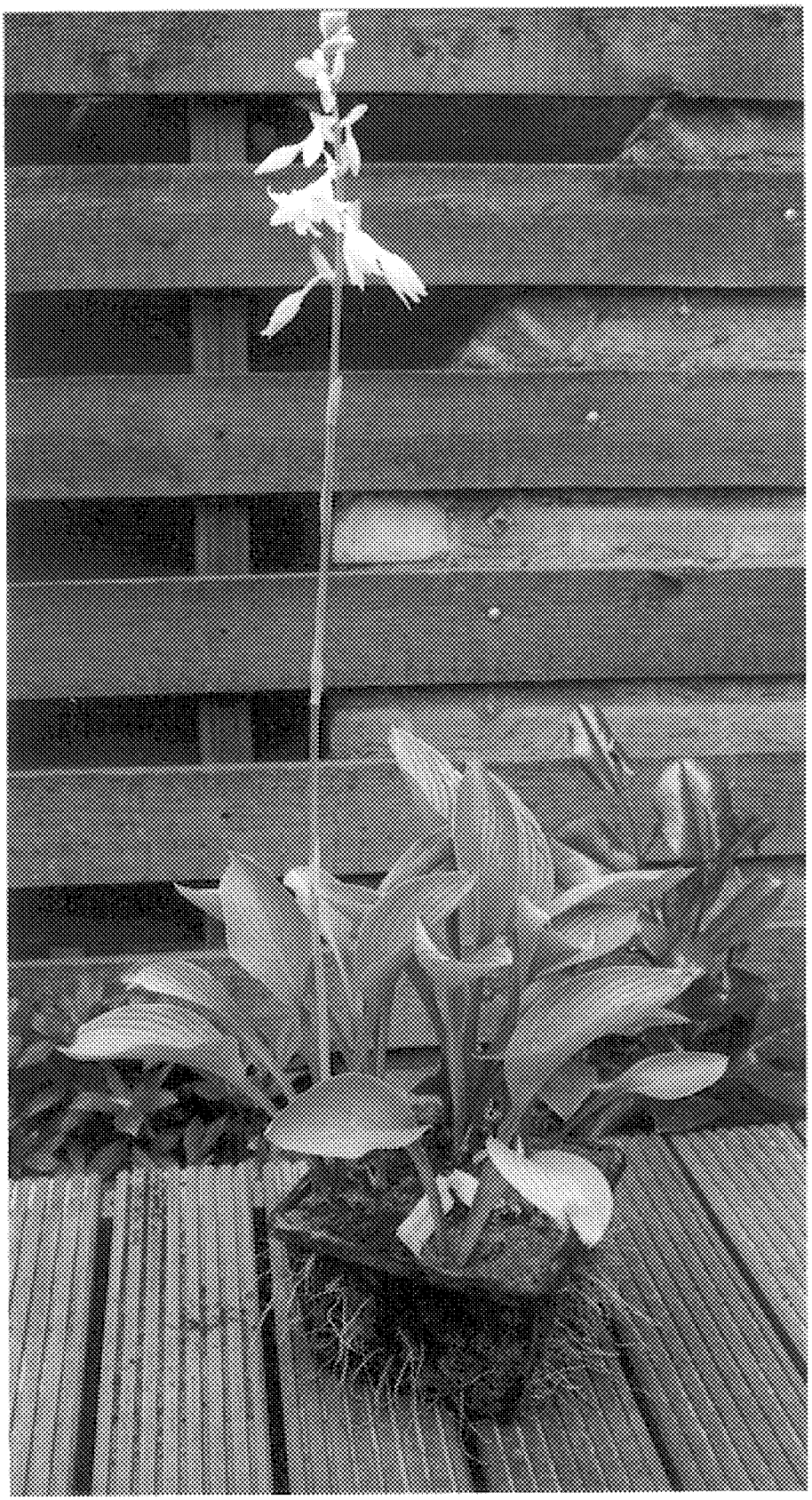

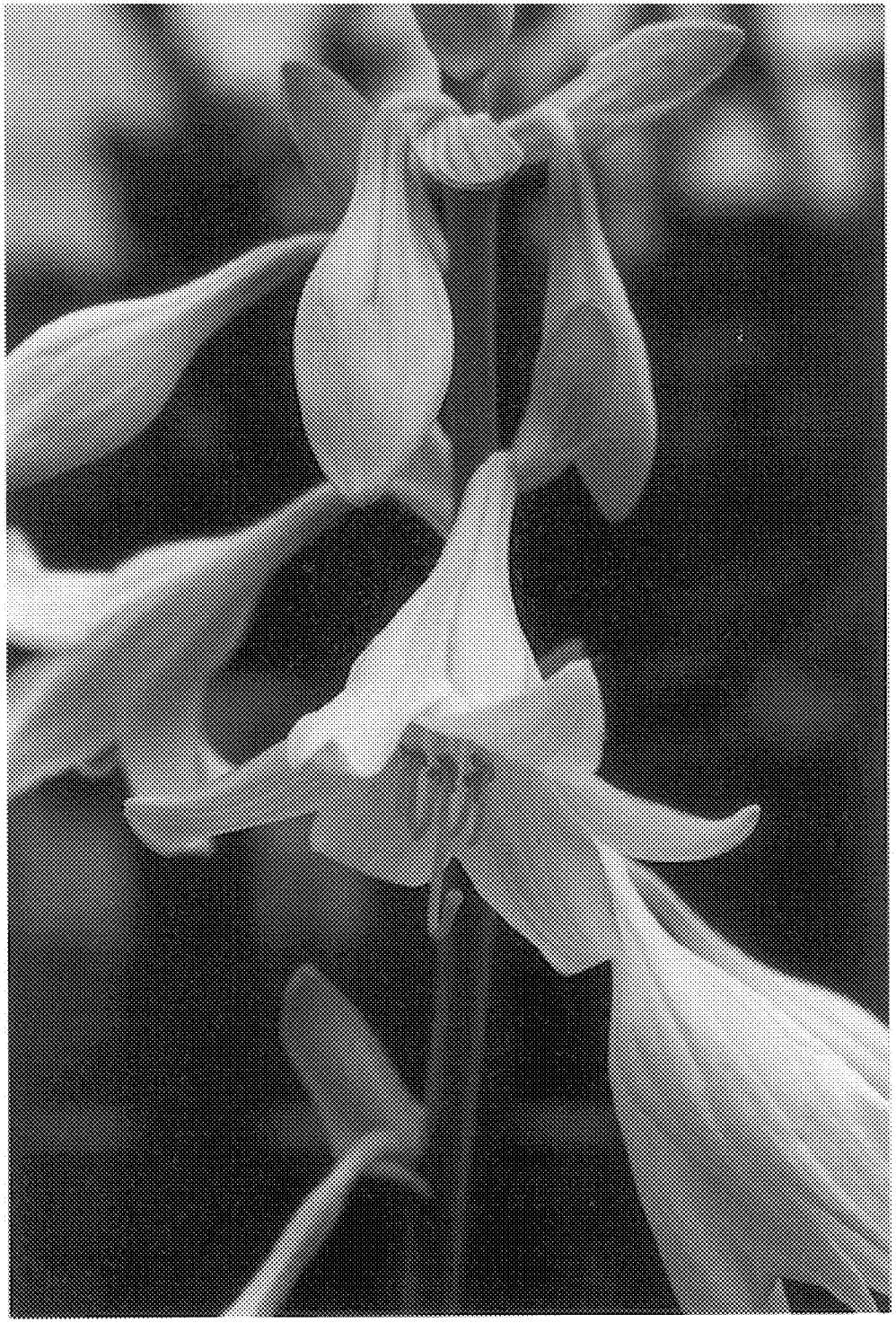

* * * * *